(12) United States Patent
Yang et al.

(10) Patent No.: US 7,519,409 B2
(45) Date of Patent: Apr. 14, 2009

(54) IMPLANTABLE CELL/TISSUE-BASED BIOSENSING DEVICE

(75) Inventors: Zhongping Yang, Woodbury, MN (US); James D. Reinke, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 313 days.

(21) Appl. No.: 11/322,117

(22) Filed: Dec. 29, 2005

(65) Prior Publication Data

US 2007/0154893 A1    Jul. 5, 2007

(51) Int. Cl.
*A61B 5/05* (2006.01)

(52) U.S. Cl. .................... 600/347; 600/345; 600/365; 600/372

(58) Field of Classification Search ............... 600/345, 600/347, 365, 372
See application file for complete search history.

(56) References Cited

U.S. PATENT DOCUMENTS

| | | | |
|---|---|---|---|
| 4,490,216 A * | 12/1984 | McConnell | 205/777.5 |
| 5,101,814 A | 4/1992 | Palti | |
| 5,133,354 A | 7/1992 | Kallok | |
| 5,146,918 A | 9/1992 | Kallok | |
| 5,158,080 A | 10/1992 | Kallok | |
| 5,174,287 A | 12/1992 | Kallok | |
| 5,190,041 A | 3/1993 | Palti | |
| 5,211,173 A | 5/1993 | Kallok | |
| 5,213,568 A | 5/1993 | Lattin | |
| 5,215,082 A | 6/1993 | Kallok | |
| 5,233,983 A | 8/1993 | Markowitz | |
| 5,238,006 A | 8/1993 | Markowitz | |
| 5,281,219 A | 1/1994 | Kallok | |
| 5,300,094 A | 4/1994 | Kallok | |
| 5,368,028 A * | 11/1994 | Palti | 600/345 |
| 5,483,969 A | 1/1996 | Testerman | |
| 5,485,851 A | 1/1996 | Erickson | |
| 5,513,636 A | 5/1996 | Palti | |
| 5,522,862 A | 6/1996 | Testerman | |
| 5,540,731 A | 7/1996 | Testerman | |
| 5,540,732 A | 7/1996 | Testerman | |
| 5,540,733 A | 7/1996 | Testerman | |
| 5,546,952 A | 8/1996 | Erickson | |

(Continued)

FOREIGN PATENT DOCUMENTS

EP       0962773 A     12/1999

(Continued)

OTHER PUBLICATIONS

David J. Christini, et al., Direct biologically based biosensing of dynamic physiological function, Am J Physical Heart Circ Physiol, 280: H2006-H2010, 2001.

(Continued)

*Primary Examiner*—Robert L Nasser
*Assistant Examiner*—Karen E Toth
(74) *Attorney, Agent, or Firm*—Carol F. Barry

(57) ABSTRACT

An implantable cell/tissue-based biosensor device detects and/or monitors the amount of one or more specific analytes within a patient. Stimulation circuitry stimulates the cells/tissue of the biosensor device causing the cells/tissue to evoke a response that is altered by the presence of a specific analyte. Sensing circuitry detects the evoked response and the amount of analyte is determined based on the detected response.

20 Claims, 7 Drawing Sheets

U.S. PATENT DOCUMENTS

| | | | |
|---|---|---|---|
| 5,549,655 | A | 8/1996 | Erickson |
| 5,591,216 | A | 1/1997 | Testerman |
| 5,593,431 | A | 1/1997 | Sheldon |
| 5,771,891 | A | 6/1998 | Gozani |
| 5,895,360 | A | 4/1999 | Christopherson |
| 5,944,680 | A | 8/1999 | Christopherson |
| 5,981,268 | A | 11/1999 | Kovacs et al. |
| 5,993,378 | A | 11/1999 | Lemelson |
| 6,006,134 | A | 12/1999 | Hill |
| 6,021,352 | A | 2/2000 | Christopherson |
| 6,044,297 | A | 3/2000 | Sheldonj |
| 6,051,422 | A | 4/2000 | Kovacs et al. |
| 6,060,640 | A | 5/2000 | Pauley et al. |
| 6,099,479 | A | 8/2000 | Christopherson |
| 6,126,611 | A | 10/2000 | Bourgeois |
| 6,132,384 | A | 10/2000 | Christopherson |
| 6,140,045 | A | 10/2000 | Wohlstadter et al. |
| 6,251,126 | B1 | 6/2001 | Ottenhoff |
| 6,266,564 | B1 | 7/2001 | Hill |
| 6,269,269 | B1 | 7/2001 | Ottenhoff |
| 6,275,717 | B1 | 8/2001 | Gross et al. |
| 6,361,531 | B1 | 3/2002 | Hissong |
| 6,409,720 | B1 | 6/2002 | Hissong |
| 6,413,254 | B1 | 7/2002 | Hissong |
| 6,455,303 | B1 | 9/2002 | Orwar |
| 6,558,345 | B1 * | 5/2003 | Houben et al. ............... 604/66 |
| 6,649,417 | B2 | 11/2003 | Greenbaum et al. |
| 6,650,919 | B2 * | 11/2003 | Edelberg et al. ............ 600/345 |
| 6,716,620 | B2 * | 4/2004 | Bashir et al. ............. 435/287.2 |
| 7,214,190 | B1 * | 5/2007 | Wilson ....................... 600/309 |
| 2002/0038083 | A1 * | 3/2002 | Houben et al. .............. 600/365 |
| 2002/0062072 | A1 | 5/2002 | Edelberg |
| 2007/0060815 | A1 * | 3/2007 | Martin et al. ............... 600/372 |

FOREIGN PATENT DOCUMENTS

EP        1588737 A     10/2005

OTHER PUBLICATIONS

Jay M. Edelberg, et al., Enhanced myocyte-based biosensing of the blood-borne signals regulating chronotropy, J Appl Physiol 92: 581-585, 2002.

J. J. Pancrazio, et al., Development and Application of Cell-Based Biosensors, Annals of Biomedical Engineering, vol. 27, pp. 697-711, 1999.

International Search Report, PCT/US2006/062144, Mar. 19, 2007, 7 Pages.

* cited by examiner

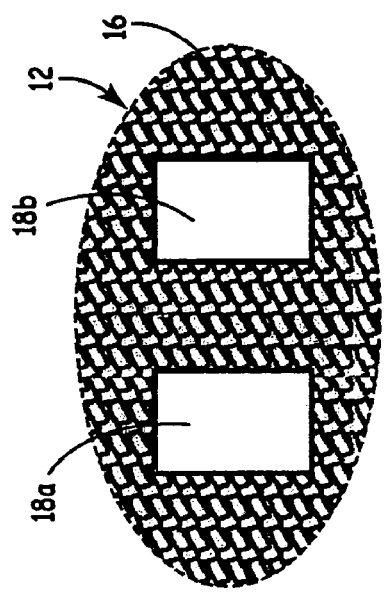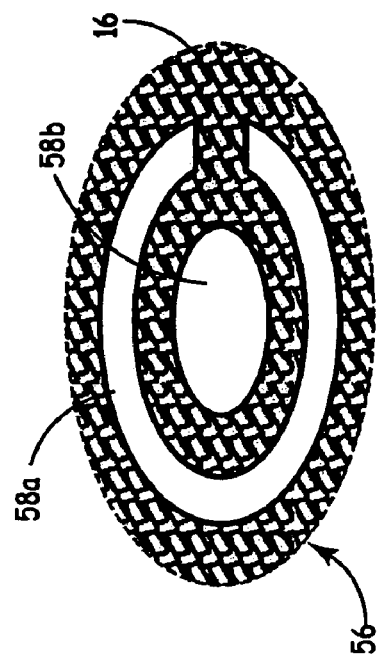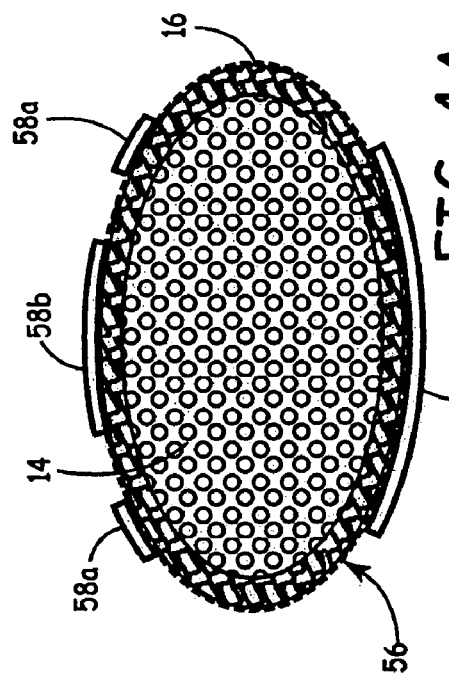

IMPLANTABLE CELL/TISSUE-BASED BIOSENSING DEVICE

FIELD OF THE INVENTION

The present invention relates to sensors for detecting an analyte in a patient. In particular, the present invention relates to implantable cell/tissue-based sensors for in vivo detection of an analyte.

BACKGROUND OF THE INVENTION

Numerous diseases and pathophysiological states are associated with deviations from normal concentrations of analytes in a patient's blood or tissues. Congestive heart failure (CHF), for instance, causes significant morbidity and mortality, and the healthcare expenditure for this disease is substantial. While in vitro diagnostic assays to measure various analyte levels in the blood are now in use, these assessments are point-in-care assessments that do not provide the clinician a complete profile of a patient's changing status. The inability to determine when a patient's CHF is worsening (before a patient gains several pounds in weight and/or edema is greatly increased) until the patient has a doctor's appointment or requires hospitalization will result in a delay of treatment. Moreover, required changes to the patient's therapy will be delayed.

Implantable biosensors have recently become an important tool for analyzing and quantifying analyte compositions in a patient's blood which could be used for initiating therapy, conducting diagnostics or monitoring. Cells and/or tissues within the patient's body may act as sensors to detect and monitor these analyte concentrations. For early detection of disease or change in disease such as CHF, it is desirable for the implantable biosensor to be sensitive to changes in analyte levels.

BRIEF SUMMARY OF THE INVENTION

The disclosure relates to a cell/tissue-based device and method for detecting and/or monitoring an analyte in a patient. A biosensing recognition element, which specifically interacts with the analyte, is implanted within the patient. Stimulation circuitry stimulates the biosensing recognition element, which evokes a response that is altered when the biosensing recognition element interacts with the analyte. Sensing circuitry detects the response and produces a sensor signal, which is related to an amount or presence of the analyte.

BRIEF DESCRIPTION OF THE DRAWINGS

FIG. 3 is a top view of a first representative embodiment of a biosensing recognition element.

FIG. 4A is a cross-sectional side view and FIG. 4B is a top view of a second representative embodiment of a biosensing recognition element.

DETAILED DESCRIPTION OF THE INVENTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

For the sake of brevity, conventional techniques related to implantable medical device telemetry, implantable medical device data processing, data communication protocols, computer network architectures, user interface generation and manipulation, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

Figure 1:
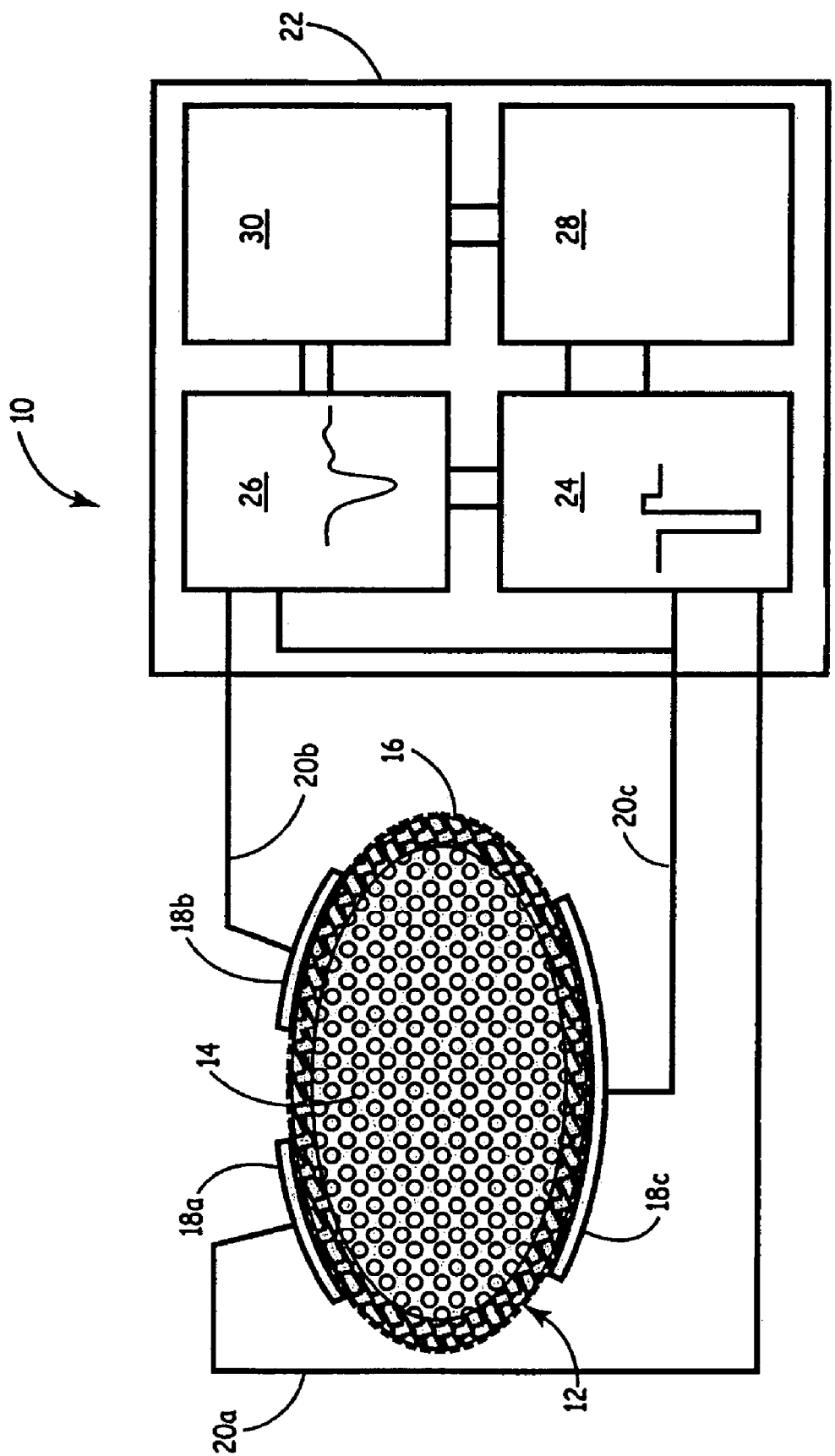
FIG. 1 is a schematic illustration of a first representative embodiment of a biosensor device.

FIG. 1 is representative embodiment of biosensor device 10. Biosensor device 10 includes biosensing recognition element 12 with biologic agent 14 and permeable membrane 16; electrodes 18a, 18b and 18c; conductors 20a, 20b and 20c; and housing 22 with stimulation circuitry 24, sensing circuitry 26, power source 28 and telemetry circuitry 30.

Biologic agent 14 is encapsulated within permeable membrane 16. Membrane 16 is a barrier to prevent cells of biologic agent 14 from migrating or being dislodged while allowing nutrients, waste products, etc. to diffuse to and from biologic agent 14. It also prevents large molecules and cells from interacting with biologic agent 14 that could result in immunological reactions and rejection of biologic agent 14.

Typically, membrane 16 is about 10 mm or less at its largest diameter. However, the size will vary depending on the analyte being monitored and the placement of element 12. Suitable materials include, for example, about 50 $\mu$m to about 100 $\mu$m thick polysulfone, polyvinylchloride/polyacylnitrile or a copolymer of polyvinyl chloride acrylic. The material should have a molecular weight cut-off no larger than about 100,000 Da but preferably about 30,000 Da to about 50,000 Da.

In some embodiments, it may be suitable to include a vascularization-promoting material on the outer surface of membrane 16. The architecture of this material promotes vascularization around biosensing recognition element 12 by allowing cellular penetration through the material. The increased vascularization creates a healthier environment for maintenance of biologic agent 14.

Electrodes 18a, 18b and 18c, which are collectively an electrical interface, are attached to the outer surface of membrane 16. Conductor 20a connects electrode 18a to stimulation circuitry 24, conductor 20b connects electrode 18b to sensing circuitry 26 and conductor 20c connects electrode 18c to stimulation circuitry 24 and sensing circuitry 26. Stimulation circuitry 24 is connected to sensing circuitry 26 and power source 28. Sensing circuitry 26 is additionally connected to telemetry circuitry 30, which, in turn, is connected to power source 28.

Device 10 may be configured with two electrodes. In this embodiment, both electrodes are shared for stimulation circuitry 24 and sensing circuitry 26. Alternatively, device 10 may be configured with four electrodes, where two electrodes are associated with stimulation circuitry 24 and two electrodes are associated with sensing circuitry 26. With the latter embodiment, a better measurement of the action potential may be obtained, because interference caused by polarization of the electrodes is reduced.

Power source 28 may be one or more batteries or another implanted medical device coupled via electrical leads, for example. Any power source adapted to provide long-term use may be used in conjunction with device 10.

Housing 22 is hermetically sealed to protect circuitry when implanted. It is initially programmed and then device 10 is implanted into a patient. Biosensing recognition element 12 is positioned in an area of the body where interaction is likely with a specific analyte for detection and/or where detection in a specific location, such as in or around the heart, is desired. Implantation of element 12 may be in patient tissue or within the patient's vascular system. Examples of analytes that may be detected by device 10 include electrolytes, hormones, amino acids/polypeptides/proteins, carbohydrates, lipids, neurotransmitters, drugs, etc. Some specific examples include glucose, lactate, creatinine, troponin T, troponin I, thrombin, B-type nutrient peptide, catecholamine, potassium, calcium, etc.

Once implanted, telemetry circuitry 30 allows device 22 to be reprogrammed as desired. Telemetry circuitry 30 may be capable of long range communication and can include a patient and/or external alert as described in commonly assigned U.S. Pat. No. 6,169,925. The alert notifies the patient or a health care facility if anaylte concentrations fall outside an acceptable range.

To detect an analyte of interest, an electrical stimulus is generated by stimulation circuitry 24 and proceeds along conductors 20a and 20c to electrodes 18a and 18c, respectively. The electrical stimulus may be any of a number of types of waveforms such as monophasic, biphasic or multiphasic electrical voltage or current pulse. The electrical stimulus then propagates across biologic agent 14. Interaction between the analyte and biologic agent 14, which is discussed in more detail below, alters depolarization and repolarization initiated by the electrical stimulus thus altering the electrical response of biologic agent 14. The electrical response detected from biologic agent 14, which can be an electrogram or impedance spectra, is detected by electrodes 18b and 18c and transmitted to sensing circuitry 26 via conductors 20b and 20c, respectively.

Typically, sensing circuitry 26 processes the data representing the evoked response. For example, one or more parameters from each action potential would be extracted to determine whether or not the parameter(s) fall within an expected range. The data would be further processed with algorithms and a microprocessor to describe the distribution of the parameter(s) and how the parameter(s) have changed over time.

The gathered and processed information is transmitted to telemetry circuitry 30 where it is stored and then transmitted to an external device and then, for example, to a healthcare facility for review. Periodic transmission would occur, for example, once a week. The Chronicle™ System and CareLink™ Network, both from Medtronic, Inc., are systems that may be used to collect and transmit the information from device 10 to a healthcare facility.

Electrically stimulating biologic agent 14 prior to detection provides a more sensitive and accurate measurement of the effect of the analyte on the electrical response. The electrical stimulus simultaneously delivers a depolarization signal to essentially all cells within biologic agent 14. Under these conditions, the maximum amount of detected electrical response is larger than without prior stimulation. Thus, the spectrum between maximum and minimum readings is wider allowing more specific and accurate correspondence between the detected readings and the concentration of analyte.

Biologic agent 14, as described above, forms the basis of biosensor device 10 and is comprised of tissue or cells. Because of its importance, sensing circuitry 26 may also be used to monitor the viability of the tissue or cells to minimize risks that altered evoked responses are due to, for example, dead or dying cells or tissue instead of the presence of an analyte. Monitoring may be carried out by varying the timing of the stimulation from stimulation circuitry 24. The time from stimulation to the action potential is then measured and used to determine if biologic agent 14 is viable.

The tissue or cells of biologic agent 14 may be any of a number of types but are typically excitable such as cardiac myocytes or neurons or are genetically modified to produce a detectable electrical response.

The cells or tissue may be derived from various animal sources but are usually human. Cells or tissue derived from the patient may also be used.

The cells or tissue may also be derived from allogeneic or syngeneic stem cells. The stem cells, which may or may not be genetically modified, are cultured to differentiate into an appropriate tissue or cell type.

The cells or tissue may be modified at a molecular, genetic and/or cellular level. Molecularly modified cells or tissue are treated either in vivo or in vitro with a component that modifies a function or activity of the tissue or cells. Such components include, for example, cytokines, growth factors and hormones.

Genetically modified cells or tissue are engineered to include stable or transient sequence that is expressed by the cells or tissue. The expressed product is typically protein. The sequence may express a product normally expressed by the cells or tissue such that the cells or tissue now overexpress the product, or the sequence may express a product that is foreign to the cells or tissue. Alternatively, the sequence may express a chimeric product that is a combination of the two or it may express a mutant/modified version of a normally expressed product.

In addition, the cells or tissue may be genetically modified to alter the level of expression of a specific gene. For example, a gene may be regulated and normally only expressed under specific conditions. Regulatory elements of the gene can be modified such that the gene is constitutively expressed.

Cellularly modified cells or tissue have altered intracellular and/or extracellular matrices or growth architecture that affect cellular activity or function. For example, cells may be cultured in specific geometric configurations such as in circular patterns.

Figure 2A:
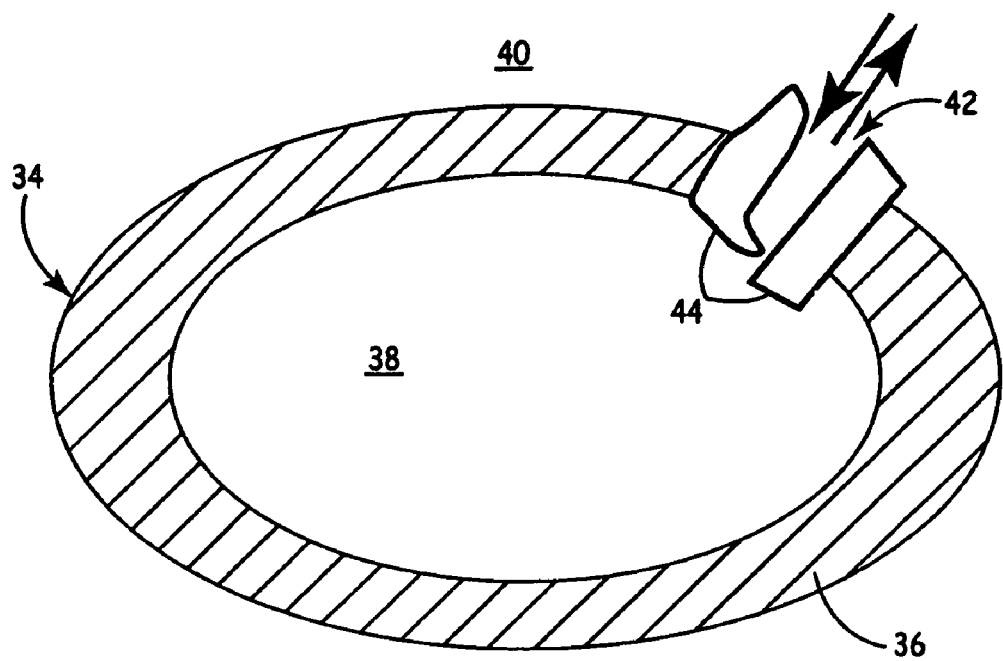
FIG. 2A-2D are schematic, cross-sectional illustrations of representative embodiments of cells that may be used with the biosensor device.

FIGS. 2A-2D illustrate representative embodiments of cells useful in device 10. FIG. 2A shows excitable cell 34. Cell 34 may, for example, be a myocardial cell or neuronal cell. Cell 34 includes membrane 36, intracellular space 38, extracellular space 40 and ion channel 42 with subunits 44. Typically, ion channel 42 transports ions from extracellular space 40 into intracellular space 38, from intracellular space 38 into extracellular space 40 or both. Transported ions may be, for example, sodium, potassium, or calcium. During the resting phase, cell 34 has an electrical charge across membrane 36, with intracellular space 38 being negative with respect to extracellular space 40. Certain external stimuli, such as the electrical stimulation described above, initiate depolarization where the charge across membrane 36 is reduced. During depolarization, ion channel 42 opens to allow an influx of ions into intracellular space 38. Depolarization of cell 34 occurs as a wave as each subsequent ion channel 42 is triggered along membrane 36. The cell subsequently repolarizes to its resting potential, and the combination of depolarization and repolarization constitute the action potential. The electrical signals generated by the action potential, as is well-known in the art, can be detected.

With respect to device 10, cell 34 is useful in detecting the effect of substances such as pharmaceutical agents or toxins. Many substances can effect cellular action potentials. In this embodiment of device 10, those effects can be monitored to indicate the effect of the substance, whether or not cells within the patient are responding appropriately or to titrate an appropriate dose of a particular substance to evoke a particular response. In addition, the effects of combining medications can be monitored.

Figure 2B:
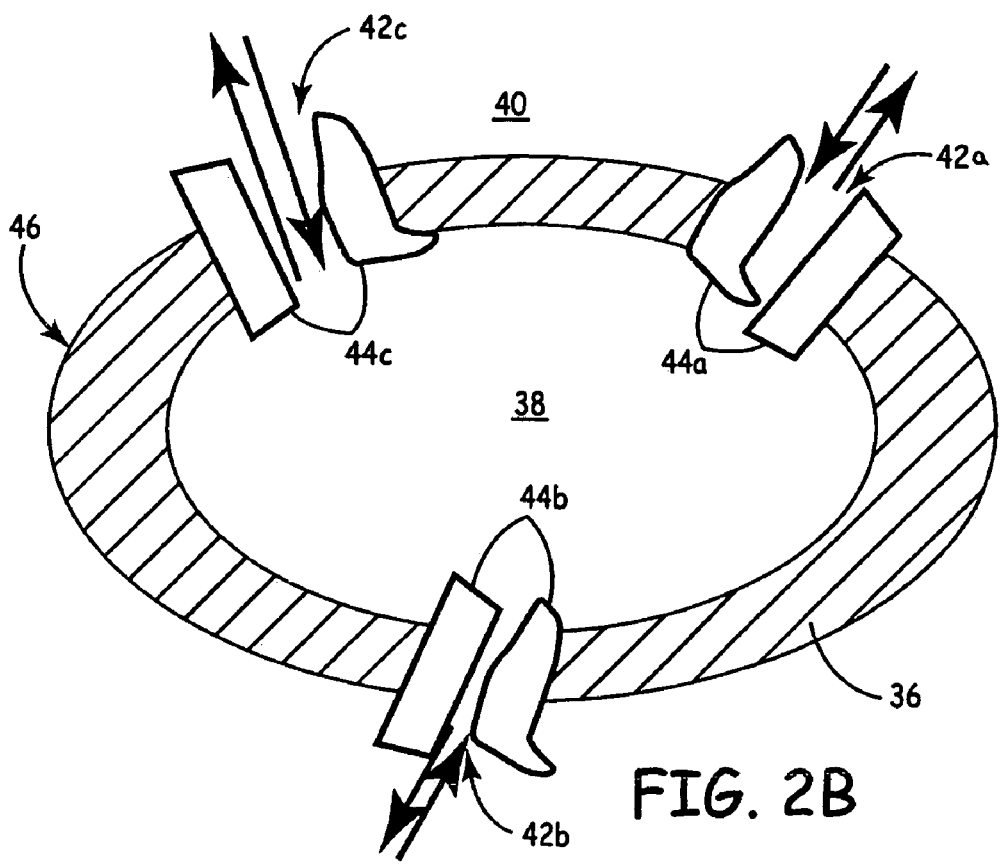

In order to increase the sensitivity of the cells or tissue, cells may be genetically modified to overexpress channel proteins such as subunits 44. FIG. 2B shows modified cell 46 having membrane 36 and ion channels 42a, 42b and 42c with subunits 44a, 44b and 44c, respectively. In this embodiment, because cell 46 has more ion channels than that of cell 46, cell 46 has greater sensitivity and creates a stronger electrical signal than that of cell 44.

Figure 2C:
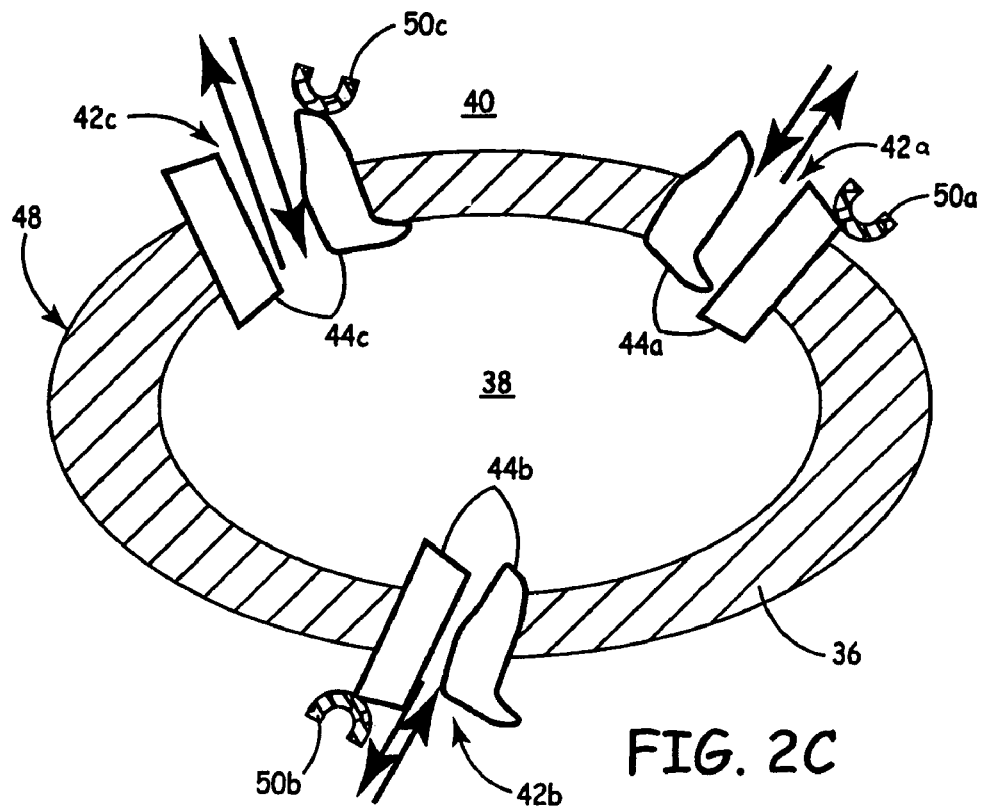
Figure 2D:
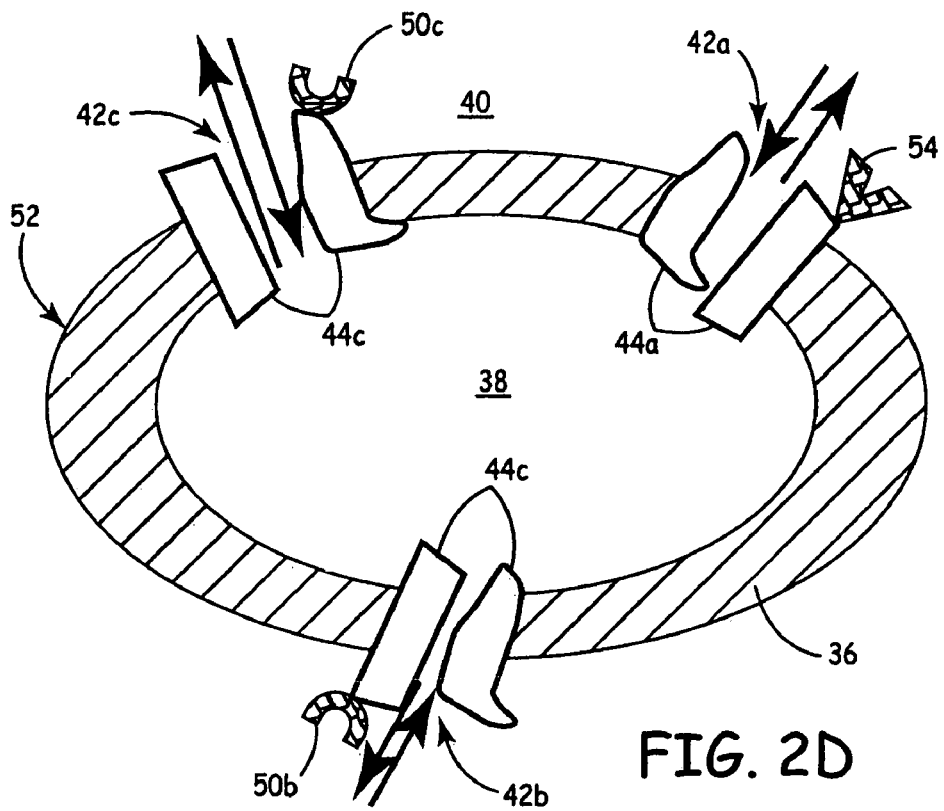

FIG. 2C is a representative embodiment of a modified cell 48. In this embodiment, ion channels 42a, 42b and 42c are not only overexpressed by cell 48, but are also modified to include analyte specific receptors 50a, 50b and 50c. The term receptors also include antibodies, antibody fragments or any type of ligand. Receptors 50a, 50b and 50c extend into extracellular space 40 for interaction with an analyte. For example, device 10 may be used to detect troponin I in vivo when receptors 50a, 50b and 50c specifically bind troponin I. When bound, ion channels 42a, 42b and 42c open allowing ion flow across membrane 36, which generates a detectable electrical signal. The concentration of troponin I directly relates to the amount of binding to one or more of receptors 50a, 50b and/or 50c and the resulting electrical signal that is evoked. By detecting and analyzing that electrical signal, the concentration of troponin I within the patient can be determined.

In some instances, it may be beneficial to detect two different or two forms of a protein. For instance, device 10 may be used to detect combined concentrations of troponin I and troponin T. A cell type represented by cell 52 in FIG. 2D may be used. In this embodiment, one of subunit 44a is now linked to receptor 54 (a troponin T specific receptor), while subunits 44b and 44c are linked to receptors 50b and 50c, respectively. In this way, a single cell type detects combined concentrations of two different proteins or two forms of the same protein.

Some examples of membrane channel proteins that are useful with the present invention are listed in Table 1. Table 1 also indicates each proteins function and the corresponding gene from which it is expressed.

TABLE 1

| Protein | Function | Gene |
| --- | --- | --- |
| sodium channel protein, cardiac and skeletal muscle alpha-subunit | voltage-dependent depolarization | SNC7A/SCN6A |

TABLE 1-continued

| Protein | Function | Gene |
| --- | --- | --- |
| voltage-gated sodium channel alpha-9/10-like | voltage-dependent depolarization | SCN9A/SCN10A |
| potassium channel Kv9.1 | voltage-dependent depolarization | KCNS1 |
| protein-tyrosine phosphatase epsilon | voltage-dependent depolarization | PTPE |
| small-conductance calcium-activated potassium channel SK3 | voltage-dependent hyperpolarization | KCNN3 |
| voltage-dependent T-type calcium channel alpha-1G subunit | voltage-dependent calcium influx | CACNA1G |
| dihydropyridine-sensitive L-type, calcium channel alpha-2/delta subunits | voltage-dependent calcium influx | CACNA2D1 |
| voltage-dependent calcium channel gamma-5 subunit | voltage-dependent calcium influx | CACNG5 |
| outward rectifying potassium channel protein TREK-1 | mechano-dependent hyperpolarization | KCNK2 |
| short transient receptor potential channel 2 | receptor-dependent calcium influx | TRP2 |
| aquaporin 1 | water influx | AQP1 |
| sodium/hydrogen exchanger 5 NHE-5 | proton efflux | NHE5/SLC9A5 |
| sodium/calcium exchanger 1 NCX-1 | calcium efflux | SLC8A1/NCX |
| plasma membrane calcium-transporting ATPase 1 | calcium efflux | ATP2B1/PMCA1 |
| cation-chloride cotransporter 6 | cation and chloride co-transport | CCC6 |
| natural resistance-associated macrophage protein | iron and manganese uptake | NRAMP1/SLC11A1 |
| amino-acid transporter ATA-3/AFTP-1 | amino acid transport | SLC38A4 |
| solute carrier family 7/cationic amino acid transporter 3 | amino acid transport | SLC7A4 |
| sodium- and chloride-dependent glycine transporter 1 | amino acid transport | SLC6A9 |
| sodium- and chloride-dependent transporter NTT4 | neurotransmitter transport | NTT4 |
| glucose transporter 3 | facilitated diffusion of sugar | GLUT3/SLC2A3 |
| glucose transporter 5 | facilitated diffusion of sugar | GLUT5/SLC2A5 |

As noted above, electrodes 18a, 18b and 18c may be attached to the outer surface of membrane 16. FIG. 3 is a top view of biosensing recognition element 12 showing electrodes 18a and 18b. Electrodes 18a, 18b and 18c are fabricated from an inert metal and therefore, may also be contained within membrane 16 and in direct contact with biologic agent 14.

In addition, electrodes of the present invention may take on various configurations. FIGS. 4A and 4B are side and top views illustrating a representative embodiment of biosensing recognition element 56. In this embodiment, electrode 18c is identical to the previous embodiment. Electrode 58a, however, is C-shaped, and electrode 58b is centered within electrode 58a. The configurations shown here are only exemplary. Any of a number of configurations may be used in conjunction with device 10.

Figure 5:
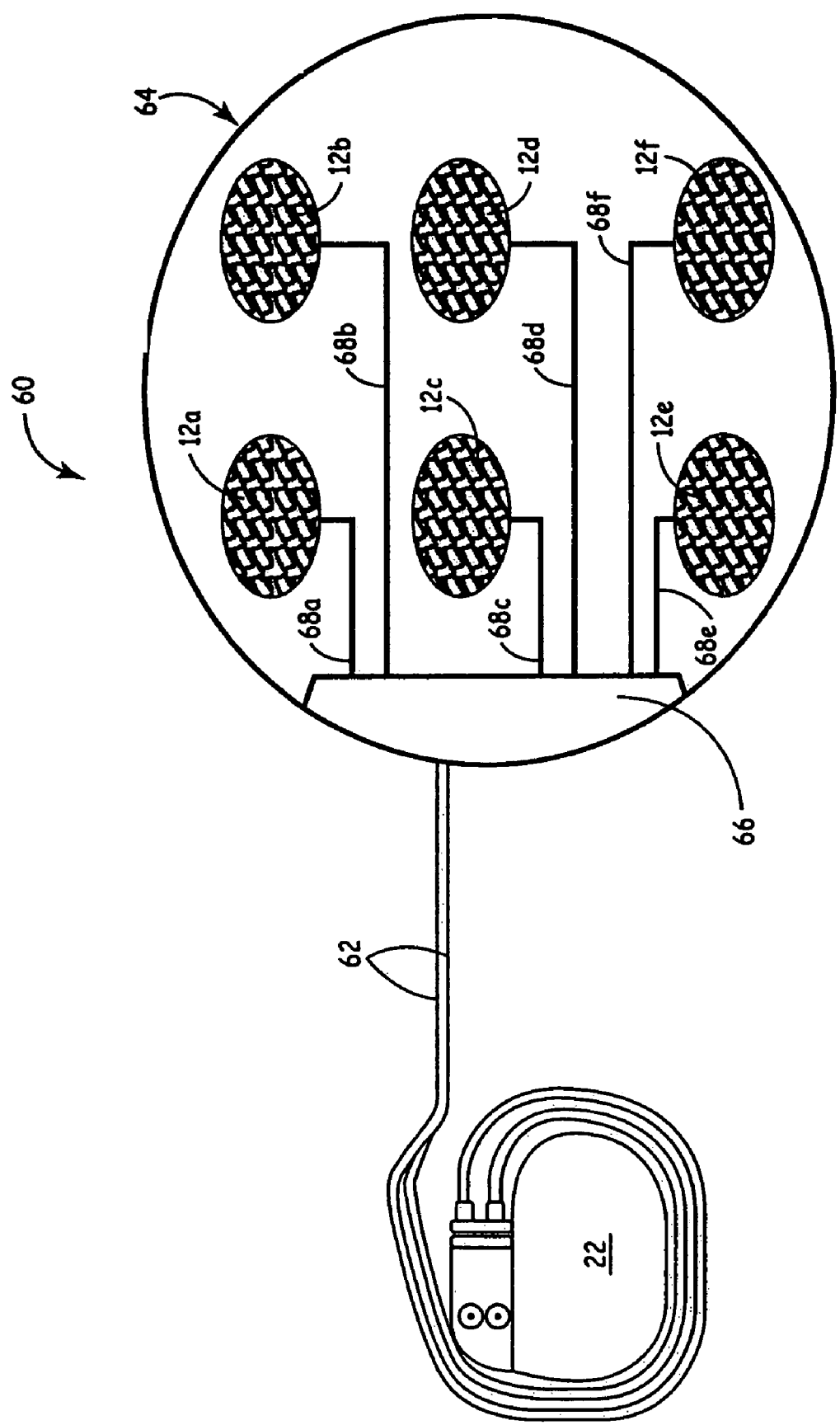
FIG. 5 is a schematic illustration of a second representative embodiment of a biosensor device.

In another variation of the present invention, an array of biosensing recognition elements 12 may be used for detecting multiple analytes. FIG. 5 is a representative embodiment of biosensing array device 60. Device 60 includes housing 22 with leads 62, which connect to array 64. Array 64 includes lead switch 66 connected to biosensing recognition elements 12a-12f via leads 68a-68f, respectively.

Biosensing recognition elements 12a-12f are each configured essentially identical to biosensing recognition element 12 shown in FIG. 1, except that each of elements 12a-12f contain a biologic agent 14 that is specific for a different analyte. Lead switch 66 allows stimulation of and detection via individual biosensing elements at specific times. Alternatively, switching between individual biosensing elements can be performed by switching circuitry within housing 22.

For example, element 12a detects analyte A, element 12b detects analyte B, etc. Device 10 can be programmed so that element 12a is stimulated and its response is sensed first. Then, element 12b is stimulated and its response is sensed second. This process continues through to element 12f. Device 10 can be programmed for any pattern of switching between biosensing recognition elements 12a-12f. In addition, array 64 can accommodate additional or fewer biosensing recognition elements as desired.

In an alternate embodiment, a single membrane 16 may encompass array 64 instead of individual membranes 16 encompassing each of elements 12a-12f. A single membrane 16 around array 64 could be easier to assemble but there would be increased risk of migration of the various biologic agents.

Figure 6:
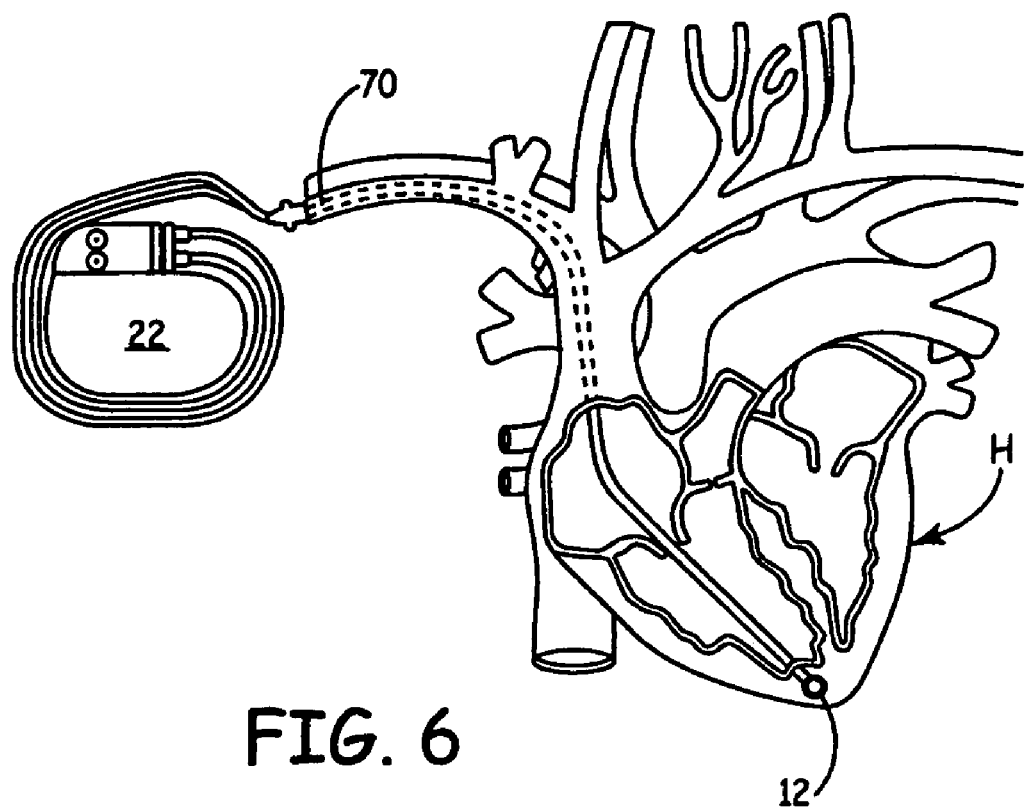
FIG. 6 is a schematic illustration of a representative embodiment of a biosensor device implanted in endocardium.

As noted previously, biosensing recognition element 12 can be implanted into any of a number of locations within a patient. FIG. 6 is a representative embodiment showing element 12 implanted into the endocardium of heart H. Leads 70 extend out of heart H to connect to circuitry within housing 22.

Figure 7:
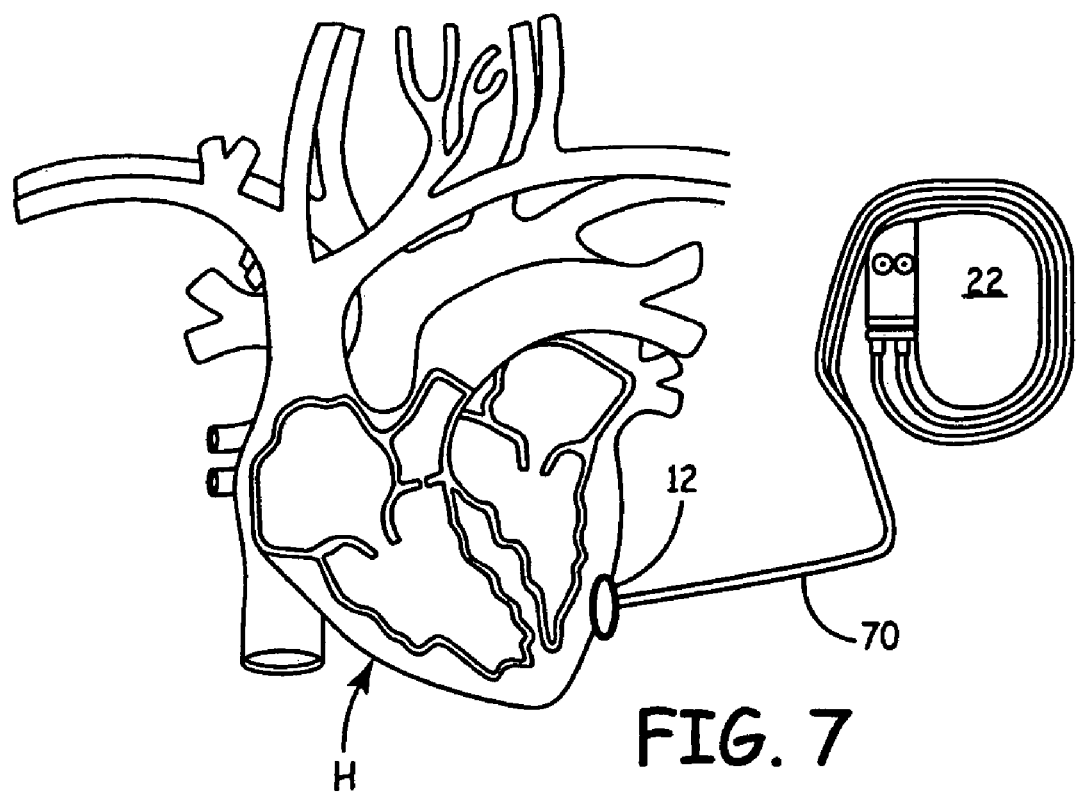
FIG. 7 is a schematic illustration of a representative embodiment of a biosensor device implanted in epicardium.

In FIG. 7, biosensing recognition element 12 is implanted into the epicardium of heart H. Again, electrodes 70 connect element 12 with circuitry within housing 22.

Figure 8:
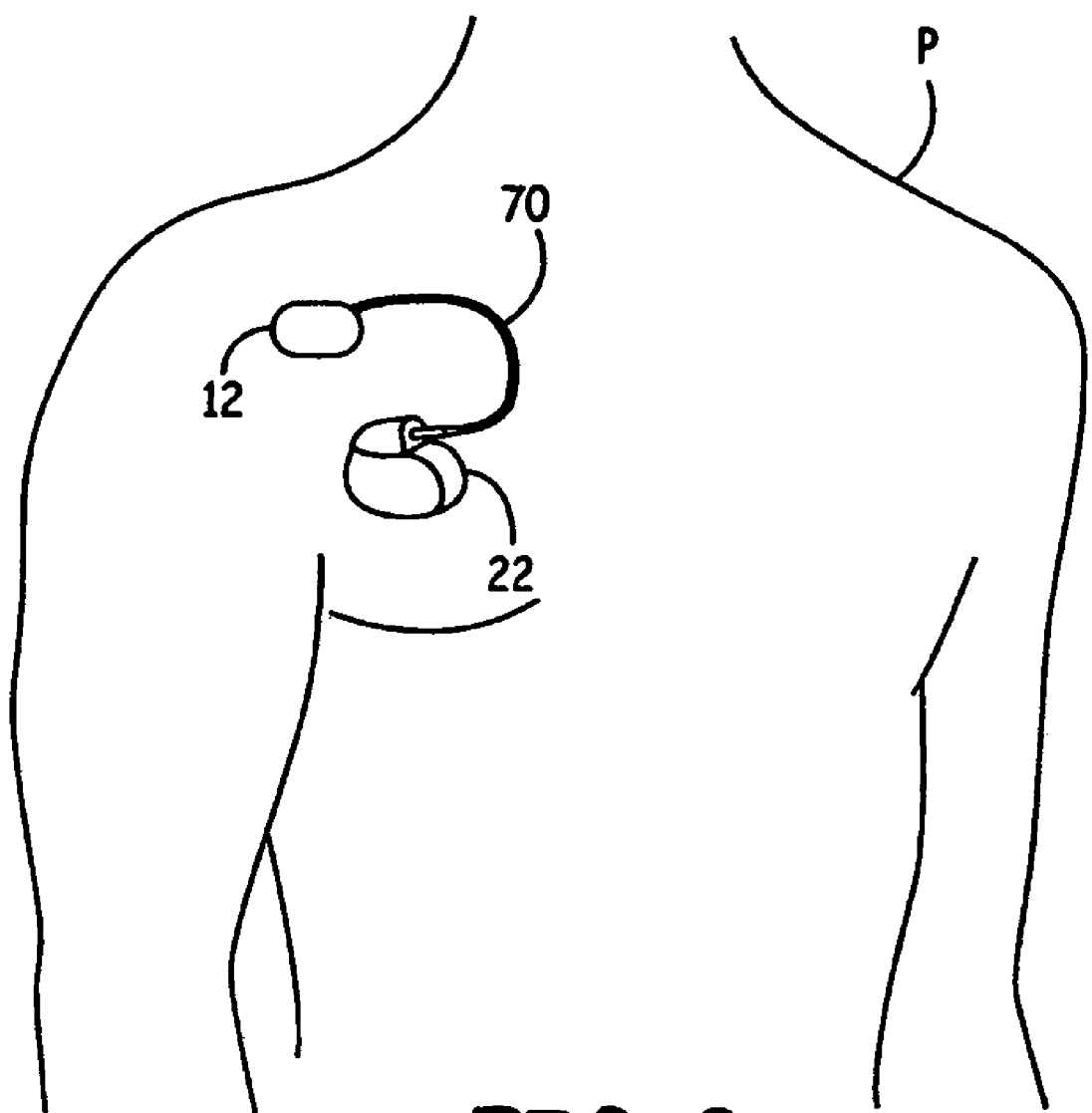
FIG. 8 is a schematic illustration of a representative embodiment of a biosensor device implanted in subcutaneous tissue.

In another representative embodiment shown in FIG. 8, biosensing recognition element 12 is implanted subcutaneously into the torso of patient P. These embodiments are exemplary. Depending on the analyte(s) being detected, element 12 could be positioned almost anywhere within patient P. In addition, housing 22 shown in any of the embodiments can contain components and circuitry for delivering therapy to patient P.

Device 10 or device 60 may be stand-alone products or be integrated as part of a therapy delivery device. Such therapy delivery devices include implantable pacemakers, defibrillators, cardiac resynchronization therapy systems, drug pumps or any other means known in the art. The integrated devices may be programmed such that patient treatment is automatically altered or initiated based on the detected analytes. Alternatively, treatment provided by the integrated devices may be altered or started by a clinician after analysis of data gathered from the integrated device.

The stimulation of cells in a cell/tissue-based sensor and detection of the evoked response provides more accurate and sensitive in vivo detection of an analyte. This not only results in earlier and/or better treatment for the patient but also potentially decreases healthcare costs. Without analyte detection, signs of disease or worsening conditions may only be seen after the disease or condition has significantly progressed to later stages making treatment longer and more difficult.

Although the present invention has been described with reference to preferred embodiments, workers skilled in the art will recognize that changes may be made in form and detail without departing from the spirit and scope of the invention.

The invention claimed is:

1. A biosensor device for sensing an analyte in a patient, the biosensor device comprising:
    a biosensing recognition element capable of interacting with the analyte and carrying out a response to electrical stimulation that is alterable upon interaction with the analyte;
    an electrical interface contacting the biosensing recognition element;
    stimulation circuitry, associated with the electrical interface, for delivering the electrical stimulation to the biosensing recognition element; and
    sensing circuitry, associated with the electrical interface, for sensing the response of the biosensing recognition element to the electrical stimulation.

2. The biosensor device of claim 1 wherein the biosensing recognition element composes:
    a biologic agent; and
    a permeable membrane encapsulating the biologic agent.

3. The biosensor device of claim 2 wherein the biologic agent is molecularly, genetically or cellularly modified.

4. The biosensor device of claim 1 wherein the response sensed by the sensing circuitry is cellular action potential, impedance or both.

5. The biosensor device of claim 1 operably connected to a therapy delivery device.

6. The biosensor device of claim 5 wherein the therapy delivery device is one of a pacemaker, defibrillator, cardiac resynchronization therapy system and drug pump.

7. The biosensor device of claim 1 wherein stimulation circuitry provides one of monophasic voltage, biphasic voltage, multiphasic voltage and current pulses.

8. The biosensor device of claim 1 and further comprising:
    telemetry circuitry in communication with the sensing circuitry.

9. The biosensor device of claim 1 wherein the biosensing recognition element further comprises a biologic agent and the sensing circuitry monitors viability of the biologic agent.

10. An implantable biosensor device for sensing a plurality of analytes, the implantable biosensor device comprising:
    a plurality of biosensing recognition elements, each biosensing recognition element capable of interacting with at least one of the plurality of analytes and carrying out a response to electrical stimulation that is alterable upon interaction with at least one of the plurality of analytes;
    a plurality of electrical interfaces contacting the plurality of biosensing recognition elements;
    stimulation circuitry, associated with the plurality of electrical interfaces, for delivering the electrical stimulation to the plurality of biosensing recognition elements; and
    sensing circuitry, associated with the plurality of electrical interfaces, for sensing the response of the plurality of biosensing recognition elements to the electrical stimulation.

11. The implantable biosensor device of claim 10 wherein each biosensing recognition element includes a biologic agent that is specific for at least one of the plurality of analytes.

12. The implantable biosensor device of claim 11 wherein the biologic agent is derived from stem cells.

13. The implantable biosensor device of claim 11 wherein the biologic agent is molecularly, genetically or cellularly modified.

14. The implantable biosensor device of claim 11 wherein the biologic agent is encapsulated in a permeable membrane.

15. The implantable biosensor device of claim 10 and further comprising:

a lead switch operably connected to the plurality of electrical interfaces.

16. A method of sensing an analyte in a patient, the method comprising:

implanting a biosensing recognition element in the patient, the biosensing recognition element being capable of interacting with the analyte and carrying out a response to electrical stimulation that is alterable upon interaction with the analyte;

electrically stimulating the biosensing recognition element;

detecting the response of the biosensing recognition element to the electrical stimulation; and relating the detected response with an amount or presence of the analyte.

17. The method of claim 16 wherein the response includes a cellular action potential or impedance.

18. The method of claim 16 and further comprising:

altering or initiating treatment of the patient based on the detected amount or presence of the analyte.

19. The method of claim 16 and further comprising:

monitoring viability of the biosensing recognition element.

20. The method of claim 16 wherein the response is implemented as a diagnostic, monitoring or both tools.

* * * * *

UNITED STATES PATENT AND TRADEMARK OFFICE
CERTIFICATE OF CORRECTION

PATENT NO. : 7,519,409 B2 Page 1 of 1
APPLICATION NO. : 11/322117
DATED : April 14, 2009
INVENTOR(S) : Zhongping Yang and James D. Reinke It is certified that error appears in the above-identified patent and that said Letters Patent is hereby corrected as shown below:

Col. 8, line 19, delete "element composes"
and insert in place thereof --element comprises:--

Signed and Sealed this

Tenth Day of November, 2009

David J. Kappos
*Director of the United States Patent and Trademark Office*